United States Patent [19]

Stoudt et al.

[11] 4,335,101
[45] Jun. 15, 1982

[54] ORAL HYGIENE ENZYMES AND METHOD FOR PREPARATION

[75] Inventors: Thomas H. Stoudt, Westfield; Karl H. Nollstadt, Clark, both of N.J.

[73] Assignee: Merck & Co., Inc., Rahway, N.J.

[21] Appl. No.: 372,137

[22] Filed: Jun. 21, 1973

Related U.S. Application Data

[63] Continuation-in-part of Ser. No. 170,642, Aug. 10, 1971, abandoned.

[51] Int. Cl.³ .......................... A61K 7/28; C12N 9/24
[52] U.S. Cl. ........................................ 424/50; 424/94; 435/200
[58] Field of Search .......................... 195/62, 65, 66 R; 424/50, 94; 435/200

[56] References Cited

U.S. PATENT DOCUMENTS 3,562,385  2/1971  Block et al. .
3,590,121  6/1971  Shiff et al. .

Primary Examiner—Lionel M. Shapiro
Attorney, Agent, or Firm—Frank M. Mahon; Hesna J. Pfeiffer

[57] ABSTRACT

Enzymes called cariogenanases, elaborated by microorganisms are isolated and characterized as polysaccharases capable of degrading cariogenan, a newly discovered glucan of dental plaque composed of $\alpha\text{-}(1\rightarrow 3)$ and $\alpha\text{-}(1\rightarrow 2)$ linkages. The enzymes are isolable from culture broths of various organisms by protein precipitation methods, and have utility as an anti-dental plaque agent, either as the sole enzymatic agent or in combination with dextranases and/or plaque dispersing proteases.

7 Claims, No Drawings

ORAL HYGIENE ENZYMES AND METHOD FOR PREPARATION

This is a continuation-in-part of copending application Ser. No. 170,642, filed August 10, 1971.

This invention relates to newly discovered enzymes useful for reducing cariogenic dental plaque, to a process for the isolation and purification of the enzymes, and to compositions comprising the novel enzymes as active ingredient.

It is well known that human dental plaque plays an important role in the development of caries, calculus, and periodontal disease, major health problems which should be preventable by proper oral hygiene.

Plaque adheres to the teeth and gingival tissues and retains its integrity, at least in part, through the agency of polysaccharides and proteins. One of these polysaccharides, a glucan, has been recognized in the prior art as dextran subject to enzymatic hydrolysis by dextranases. The incorporation of dextranases in oral hygiene products has been proposed in U.S. patent application Ser. No. 10,983 by Woodruff et al. Similarly, the use of plaque dispersing proteases for oral hygiene has been proposed by Mollé in *J. So. Calif. Dent. Assn.*, 35, 391 (1967) and by Shaver et al. in *J. Periodontology*, 41, 33 (1970).

It has been discovered, by the applicants that dental plaque contains another discrete glucan in amounts about equal to dextran, refractory to the hydrolytic action of dextranase, for which the name "cariogenan" has been coined.

There has now been discovered by applicants previously unreported enzymes capable of enzymatically degrading the cariogenan constituent of dental plaque. These enzymes have been named "cariogenanases".

Because of the ability of cariogenanases to degrade cariogenan, which is one of the adhesive agents of dental plaque, it finds utility as a constituent in oral hygiene products such as tooth pastes, mouthwashes, rubbing ointments, or in chewing gums, lozenges, chewable tablets, foods, beverages, or in a high velocity jet stream of water, either as the sole enzymatic constituent or as a useful adjunct in combination with other enzymes such as dextranase and/or plaque dispersing proteases.

The oral hygiene products should be constituted so that a signal oral treatment would expose the mouth to 10–20,000 units of cariogenanase, and one to several applications per day are desirable.

When used in combination with either dextranases or plaque dispersing proteases or both, the oral hygiene products should be constituted so that a single oral treatment would expose the mouth to about 100–200,000 units of dextranase, about 0.8–400 azocasein units of plaque dispersing protease, and about 10 to 20,000 units of cariogenanase as mentioned above.

The most preferred dosage for a single oral treatment is about 2,000 to 8,000 units of cariogenanase, 13,000 to 50,000 units of dextranase, and 10 to 100 units of protease.

Human dental plaque was isolated from a number of volunteers by physical scraping of the teeth and was found to contain on a dry weight basis from about 0.6 to about 2.5% of dextranase-refractory polysaccharide.

The same polysaccharide, along with dextran, was shown to be elaborated, in vitro, by *Streptococcus mutans* SL-1 (NRRL No. B-5304) when grown in a medium containing sucrose as the carbohydrate source, and also when a cell-free *Streptococcus mutans* broth containing extracellular enzymes was incubated with a sucrose solution.

In each case the cariogenan was separated from the accompanying dextran by incubation with dextranase. The cariogenan was further purified by deproteinization by standard procedures.

The structure of the cariogenan was determined by standard procedures involving partial acid hydrolysis followed by qualitative and quantitative analysis of the oligosaccharidic fractions produced thereby and by metaperiodate oxidation and borohydride reduction studies. The structure was thus determined to be an unbranched glucan possessing $\alpha\text{-}(1\rightarrow3)$ and $\alpha\text{-}(1\rightarrow2)$ links in a ratio of about 3:1.

Microbial organisms capable of enzymatically hydrolysing cariogenan are isolated from air-borne bacteria by exposing agar plates containing an appropriate nutrient medium including cariogenan as a carbohydrate source and incubating the resultant cultures at a suitable temperature, usually 28°–37° C. for up to about 10 days. Organisms found active are subcultured on similar agar plates for purposes of isolation.

The extracellular enzyme, cariogenanase is produced in isolatable quantity by incubating a culture of a cariogenanase elaborating microorganism at a suitable temperature, usually 28°–37° C. in a nutrient medium in shake flasks until a satisfactory level of cariogenanase activity is produced, usually for about 72 to about 96 hours. Generally the microorganisms do not require cariogenan as a carbohydrate source in the nutrient medium for the elaboration of cariogenanase. One of the organisms Bacillus sp. MB-2665 (NRRL No. B-5300) used to exemplify this invention did require cariogenan as a nutrient. However, by conventional mutation techniques, a constitutive mutant can be produced which does not require cariogenan in the medium.

The enzyme is isolated from the broth by clearing it of cellular debris and other insolubles by centrifugation or filtration, concentrating the centrifugate about five to fifteen fold, preferably about ten fold in vacuo, and precipitating the protein by standard procedures such as with an organic solvent, by metal complexing, or by saturation with a salt such as ammonium sulfate or the like. It is preferable to use multiple precipitations with intermediate dissolutions of the precipitate in a buffer solution and clarification of the resultant solutions by filtration or centrifugation. The final precipitate in aqueous solution is then dialyzed and kept either as a cold solution or in lyophilized form.

The enzyme thus produced was characterized in being specific for an $\alpha(1\rightarrow3)$ glucosidic linkage with a vicinal $\alpha(1\rightarrow2)$ glucosidic linkage. It has an isoelectro focusing point of 5.1. It has a broad-range pH optimum with peak activity at pH 6.0. These characteristics clearly distinguish cariogenase from any art recognized polysaccharase.

The following provides details for the various procedures used for isolation and characterization of in vivo and in vitro cariogenan and examples for the preparation and characterization of the novel enzymes of this invention, cariogenanases.

ISOLATION OF CARIOGENAN FROM HUMAN DENTAL PLAQUE

Fresh plaque was taken from donors who had stopped all oral hygiene during the plaque build-up period for 4–6 days. A small spatula was used to collect and combine plaque from all available tooth surfaces. The wet plaque, usually the size of a pea, was suspended in about 10 ml. of distilled water and the suspension placed in a boiling waterbath for 20 minutes to inactivate enzymes. The insolubles were collected by centrifugation, resuspended in about 2 ml. of distilled water, and freeze-dried. Usually, from 6-15 mg. of dry weight of plaque was obtained per donor.

The cariogenan was isolated from the plaque as follows:

The polysaccharides (10 gm.) were extracted at room temperature with 1 liter of 0.5 M NaOH with constant stirring for 30 minutes. The insolubles were removed by centrifugation and discarded. The slightly opaque supernatant was brought to pH 5.1 by adding 2 N acetic acid, with formation of a heavy gel. The volume of the very viscous suspension was noted and 200 units/ml. of dextranase was added. The suspension was incubated at 37° C. until the anthrone-positive sugars, solubilized by the dextranase, had reached a maximum level. This usually required from 6 to 8 hours. The dextranase digest which had become less viscous, was centrifuged to collect the undigested materials. The pelleted materials were washed twice in 10 volumes of distilled water. They were solubilized in 5 volumes of 0.5 N NaOH and deproteinized with an equal volume of chloroform:butanol (9:1 v/v) in a blender at low speed for 15 minutes. The chloroform-protein complex was removed by separation of the phases in the centrifuge. The clear aqueous layer was recovered by siphoning, and the deproteinization step repeated until the chloroform-protein complex appeared as a thin skin partially covering the interphase. The clear and almost colorless aqueous phase was dialyzed overnight against running deionized water. On loss of alkalinity, cariogenan settled out as a white, translucent gel, consisting of flat, shiny particles. The gel was freeze-dried to a fluffy, shiny powder, representing about 25% weight of the starting crude polysaccharide.

PREPARATION OF CARIOGENAN BY STREPTOCOCCUS MUTANS IN VITRO

The starting material in the isolation of cariogenan was produced in a medium of the following composition: 5 gm. yeast extract, 11 gm. Trypticase, 60 gm. sucrose, 1 gm. $Na_2CO_3$, 0.5 ml. salt solution ($MgSO_4.7H_2O$; 800 mg.; $FeCl_3.6H_2O$; 40 mg.; $MnCl_2$:18 mg. per 100 ml. deionized water) dissolved in 1 liter of 0.1 M phosphate buffer, pH 7.3. The medium was inoculated with Streptococcus mutans SL-1 (NRRL No. B-5304) and the insoluble material was harvested when the pH had dropped to about 5.2. Following centrifugation, the material was washed twice with 20 volumes of deionized water and freeze-dried.

Cariogenan was isolated from the freeze-dried, in vitro-produced insoluble crude polysaccharides by the same procedure as that used for isolating cariogenan from human dental plaque described previously.

PREPARATION OF CARIOGENAN BY CELL-FREE STREPTOCOCCUS MUTANS BROTH IN VITRO

Polysaccharides were produced by the addition of 5 ml. of cell-free Streptococcus mutans SL-1 broth harvested at pH 5.2, to 25 ml. of a 6% (w/v) sucrose solution (in 0.10 M phosphate buffer, pH 7.0), filtering the mixture through a 0.45 micron pore filter and incubating at 37° C. for 7 days. The polysaccharides were collected by centrifugation, washed twice in 12 ml. of distilled water, resuspended in about 2 ml. of distilled water and freeze-dried.

The cariogenan was isolated by the previously described technique.

STRUCTURE DETERMINATION OF CARIOGENAN

(a) Infra-red spectroscopy

The infra-red spectrum of cariogenan in Nujol revealed a peak at 840 $cm^{-1}$ indicating an $\alpha$-configuration of the glucosidic linkages. A complete absence of absorption at 890 $cm^{-1}$ indicates a lack of $\beta$-glucosidic linkages.

(b) Acid Hydrolysis

Cariogenan was hydrolyzed in 2 N $H_2SO_4$ (10 mg/ml) for about 48 hours. Neutralization with $BaCO_3$ and centrifugation gave a clear solution. Paper and thin layer chromatography of the solution showed glucose to be the only monosaccharide present.

Thin-layer chromatography was carried out on Silica gel G plates, (Analtech, Inc.) in two systems. System I: n-butanol:acetone:water, 4:5:1. System II: n-butanol:acetic acid:water:ethyl-ether, 9:6:1:3. The developed plates were allowed to dry in a stream of air. Residual butanol and acetic acid were removed by placing the plates in a desiccator in vacuo for 30 minutes. The sugars were located by spraying the developed plate with either a 5% solution of silver nitrate (heating at 110° C. for 10 minutes) or naphthol resorcinol reagent with heating at 100° C. for 15 minutes. A dextranase digest of linear dextran-100 (Sigma), as well as dextrose and raffinose, were used as reference markers for the estimation of the molecular size of the hydrolysis products resulting in the action of cariogenanase on cariogenan.

Paper chromatography of enzymatic and acid-hydrolysis products were carried out on Whatman No. 1 paper sheets about 20×55 cm. by the descending method. Chromatograms were developed for 2½ days with n-butanol:pyridine:water, 6:4:3. The sugars were located by staining with silver nitrate in acetone (Trevelyan, W. E., et al., Nature, 166, 444 (1960)).

(c) Partial acid hydrolysis

Cariogenan was subjected to acid hydrolysis by treating 300 mg. of it in 3 ml. of 66% sulfuric acid at ambient temperature for 15 minutes. The hydrolysate was neutralized with $Ba(OH)_2$ and diluted to 100 ml. with distilled water. After removal of $BaSO_4$, excess $Ba(OH)_2$ was removed as $BaCO_3$ by adding small pieces of dry ice. $BaCO_3$ was removed by centrifugation. The clear solution was concentrated 10-fold.

Paper and thin layer chromatography of the concentrate revealed the presence of nigerotriose (O-$\alpha$-D-glucopyranosyl-(1→3)-O-$\alpha$-D-glucopyranosyl-(1→3)-O-$\alpha$-D-glucopyranose); nigerose (O-$\alpha$-glucopyranosyl-(1→3)-O-$\alpha$-D-glucopyranose); kojibiose (O-$\alpha$-D-glucopyranosyl-(1→2)-O-$\alpha$-D-glycopyraonose) and glucose.

There was no evidence of isomaltose or isomaltotriose (1→6-linked oligosaccharides).

(d) Periodate Oxidation

Periodate oxidation studies were carried out by a modified Smith degradation as described by Misaki et al., *Agr. Biol. Chem.*, 32, 432 (1968), in studies of dextran.

The total glucose content of cariogenan as determined by the anthrone test, was 5.54 micromoles of anhydroglucose per milligram of polysaccharide. It consumed 1.53 micromoles of periodate per milligram (5.54 micromoles of anhydroglucose). On completion of the periodate oxidation, only 0.05 micromoles of formic acid per milligram of dry weight was released.

(e) Borohydride Reduction

A suspension of cariogenan was subjected to a partial Smith degradation. The resultant poly-aldehyde on reduction with sodium borohydride did not yield a soluble poly-alcohol.

Analysis of the poly-alcohol for total dextrose by the anthrone test, showed 3.8 micromoles of glucose per milligram of poly-alcohol.

Hydrolysis of the poly-alcohol failed to release any erythritol, but did produce glycerol.

(f) Conclusion

From the above evidence cariogenan was determined to be a linear glucan of $\alpha$-(1→3) linkages with intermittent $\alpha$-(1→2) linkages in a ratio of about 3:1.

EXAMPLE 1

Determination of Cariogenanase

Screening for microbial organisms producing enzymes which hydrolyze cariogenan was carried out on agar plates prepared with a defined medium containing cariogenan as a source of carbohydrate. The agar medium was composed of the following: 100 mg. of Trypticase, 1.5 g. of agar, 200 mg. of cariogenan, 0.1 ml. of a salt solution of the composition described above for the streptococcal medium; in 100 ml. of 0.1 M phosphate buffer at pH 7.0. The medium was autoclaved for 15 minutes. With the cariogenan well suspended, about 10 ml. of the medium was poured per 100×20 mm Petri dish. After exposure to air-born microorganisms, the dishes were kept at 28° C. for 10 days. The production of a hydrolytic enzyme was easily spotted by the clearing of the background of agar-suspended cariogenan around the culture. Several organisms were found active, as determined by the extent of clearing of the background of agar-suspended cariogenan. These were subcultured on similar agar plates for purposes of isolation and were found to include, an unidentified fungus (MF-4490) NRRL No. 5305; Streptomyces sp. (MA-4226, 4227, 4228, and 4229) NRRL Nos. 5306, 5307, 5308 and 5309 respectively; Bacillus sp. (MB-2793, 2794, 2796 and 2665), NRRL Nos. B-5301, B-5302, B-5303 and B-5300 respectively; and a Corynebacterium sp. (MB-2795), NRRL No. B-5310. The Bacillus sp. MB-2665 culture, NRRL No. B-5300 was selected as the organism for purposes of exemplifying this invention although any one of several others could have been employed.

Bacillus sp. MB-2665 was subcultured on cariogenan-containing agar plates prepared as described in the above procedure for the purpose of isolation and preparation of L-tubes for storage.

Example 2A

Production of Cariogenanase with Cariogenan as Carbohydrate Source

Production of cariogenanase was carried out in 2-liter unbaffled flasks containing 400 ml. of medium of the following composition: 800 mg. of nutrient broth, 800 mg. of yeast extract, 800 mg. of Trypticase, 0.20 ml. of salt solution (same as above), 8 gm. of cariogenan (not essential for all cultures); in 400 ml. of 0.1 M phosphate buffer, pH 7.0. After autoclaving (15 min. at 121° C.), the medium was inoculated with 1 ml. of a 48 hour seed culture brough up in 50 ml. (250-ml. shake-flask) of a dextrose medium, composed as follows: Aradamine (autolyzed yeast from Yeast Products, Inc.), 10 gm.; dextrose, 10 gm.; $KH_2OP_4$, 180 mg.; $Na_2HPO_4$, 190 mg.; $MgSO_4.7H_2O$, 50 mg.; dissolved in 1 liter of distilled water. The production culture (MB-2665) was incubated at 37° C. on a shaker at 200 RPM with a 2" throw. The culture was harvested when the suspended cariogenan had cleared, usually between 72 and 96 hours.

EXAMPLE 2B

Production of Cariogenanase without Cariogenan as Carbohydrate Source

A lyophilized tube of Bacillus sp. NRRL B-5301 was suspended in 2 ml. of yeast extract-dextrose medium (1% yeast extract plus 1% dextrose). This suspension was used to inoculate by streaking a series of slants composed of yeast extract-dextrose agar. The slants were incubated for 5 days at 28° C. One of the cultivated slants was washed with 10 ml. of fermentation medium and this wash was used to inoculate 50 ml. of the same fermentation medium in a 250 ml. Erlenmeyer flask. The fermentation medium was composed of 1% yeast extract, 0.5% $K_2HPO_4$, 0.1% $MgSO_4.7H_2O$ and 1% dextrose in water, pH 7.3 and was autoclaved 15 min. at 121° C. The incubation was conducted for 72 hours at 28° C. on a rotary shaker at which time assay for cariogenanase showed peak activity.

EXAMPLE 3

Isolation of Cariogenanase

The broth from Example 2A was cleared of cells and other residual insolubles by centrifugation at 2° C. for 20 minutes, 16,000×g. The clear supernatant was concentrated in vacuo (400 ml. to 40 ml.), and acetone at −60° C. was added to the concentrate in an ice-bath with stirring in 2-3 ml. portions to a final concentration of 60% (vol/vol). The precipitated materials were collected by centrifugation, 1500×g. for 10 minutes at −20° C. The precipitate was immediately suspended in 200 ml. of ice-cold 0.05 M phosphate buffer, pH 7.0. The resulting suspension was stirred for 60 minutes and then cleared of insolubles by centrifugation at 13,000×g. for 20 minutes at 2° C. The clear, pale yellow supernatant was then brought to saturation with respect to $(NH_4)_2SO_4$. The precipitate was collected by centrifugation at 13,000×g. for 20 minutes at 2° C. The precipitate was dissolved in 40-60 ml. of ice-cold distilled water and dialyzed for 24 hours. The clear solution was freeze-dried. The resulting material (yield: 150-200 mg.) assayed for 400-550 units/mg. cariogenanase activity.

EXAMPLE 4

Isoelectrofocusing of Cariogenanase

The isoelectrofocusing determination was conducted on a LKB electrofocusing column of 110 ml. capacity as described by Chaiet et al, *Applied Microbiol*, 20, 421 (1970), and was determined to be 5.1.

EXAMPLE 5

Unit Activity of Cariogenanase

Unit activity of cariogenanase was based on the observation that a straight-line relationship exists for a plot of percent clearing of a suspension of cariogenan versus the logarithm of time. With excess substrate the slope of the straight-line reflects the enzyme activity. By serial dilutions of a given enzyme preparation it was possible to construct a standard curve, plotting the slope versus an arbitrary linear scale of unit activity. The standard system of assay contained 3.25 mg. of suspended cariogenan (1.0 mg/ml of 0.05 M phosphate buffer at pH 6.0) and 0.50 ml. of enzyme diluted to a lever of activity that resulted in a slope of 4 to 22 over a 5-hour incubation period. With higher levels of enzyme the slope becomes limiting. Incubations were carried out at 37° C. in stoppered cuvettes placed on a rotating incubator, optical density readings were made at 620 m$\mu$ at zero time, 1, 3, and 5 hours. In a non-linear assay system, for example, a slope of 5 equals 6 units/ml., of 10 equals 16 units/ml., and of 20 equals 62 units/ml.

EXAMPLE 6

Optimum pH for Cariogenanase Activity

The pH optimum for cariogenanase was determined under the usual assay conditions by noting the percent dispersion of cariogenan suspensions appropriately buffered (0.1 M Sorensen buffer) over a pH range from 4.9 to 8.0. The percent dispersion was plotted versus the logarithm of time (in minutes) and the slopes determined from the resulting straight lines.

| pH Optimum of Cariogenanase Percent Dispersion of Substrate | | | | |
|---|---|---|---|---|
| pH | 15 Min. | 30 Min. | 240 Min. | Slope |
| 4.9 | 5.0 | 11.0 | 35.0 | 28.3 |
| 5.5 | 8.0 | 14.0 | 42.0 | 33.0 |
| 6.0 | 12.2 | 18.0 | 45.0 | 36.0 |
| 6.5 | 10.0 | 16.0 | 43.0 | 34.0 |
| 7.0 | 9.0 | 15.0 | 40.0 | 33.5 |
| 8.0 | 7.2 | 13.0 | 31.9 | 23.1 |

Cariogenenase has a broad-range pH optimum with peak activity near pH 6.0.

EXAMPLE 7

Linkage Specificity of Cariogenanase

The linkage specificity of the enzyme was determined by analysis of the hydrolysis products. The average length of the sugars was estimated by obtaining the ratio of total dextrose before and after reduction with NaBH$_4$. Glucose arising by the action of the enzyme was determined with glucose-oxidase (Worthington Glucostat). Thus the average length of the oligosaccharides was determined as 6.42 glucose units. These fragments would have experienced either an enrichment or a depletion of the $\alpha$-(1→2) linkages, depending on the specificity of the enzyme. It was determined that the periodate susceptibility of the inner structure (4.42 glucose units) increased from about 25 to 45%. Deduction from these findings indicate that the $\alpha$-(1→2) linkage remains intact and that the $\alpha$-(1→3) linkage is attacked by the enzyme. In addition, it was noted that approximately as many $\alpha$-(1→3) linkages were hydrolyzed by the enzyme as the total of $\alpha$-(1→2)-linkages in the glucan. It is speculated that the $\alpha$-(1→2)-linkage plays a role in specificity of the enzyme by way of recognition of the site of attack of an $\alpha$-(1→3)-linkage since the disaccharides, kojibiose and nigerose, are products of acid hydrolysis, and nigerotriose is an end-product of enzymatic hydrolysis, and nigerose, as well as nigeran, are not substrates for cariogenanase.

EXAMPLE 8

Toothpaste or Tooth Powder

Accepted formulations of the kind to be found in text books or on the market are supplemented with 5–10,000 units of cariogenanase enzyme per gram of the formulation. This would be used in the normal manner on a tooth brush, about 2 gms. of tooth-paste being used in each treatment.

EXAMPLE 9

Rubbing Ointment or Lotion

Accepted formulations of the kind to be found in text books or on the market are supplemented with about 10–20,000 units of cariogenanase enzyme per gram of the formulation. This would be applied to the teeth and gums as with the fingers.

EXAMPLE 10

Mouthwash

Accepted formulations of the kind to be found in text books or on the market are supplemented with cariogenanase concentrations of about 1.0–2,000 units per milliliter of the formulation. This would be swished about in the mouth in the usual manner, estimating the average volume employed to be 10 ml.

EXAMPLE 11

Chewing Gum

Accepted formulation of the kind to be found in text books or on the market are supplemented with 2.5–5,000 units of cariogenanase enzyme per gram of the formulation, as an ordinary chewing stick weighs about 4 grams. A chewing gum stick, for instance, would be chewed in the usual manner. In like manner, a chewable tablet could be employed.

EXAMPLE 12

Lozenge

Accepted formulations of the kind to be found in text books, or on the market are supplemented with 10–20,000 units of cariogenanase per lozenge. The lozenge would be dissolved slowly in the mouth in the normal manner. This is the most preferred type of formulation in that the normal manner of use provides the longest contact time between the active enzyme and the plaque.

EXAMPLE 13

Food

As large amounts of food are generally consumed, from about 1–2000 units of cariogenanase enzyme would be added to a gram of the food such as breakfast cereal and breads for example.

Other examples of especial value are the addition of the enzyme to foods containing high amounts of sucrose such as ordinary candy and ice cream. Mastication in the usual manner applies the enzyme to the teeth and gums.

EXAMPLE 14

Beverages

The enzyme can be added to drinking water or milk but it is of especial value in sucrose containing beverages such as cola, orange and the like flavored drinks containing sucrose and/or artificial sweeteners. It would be added in the amount of about 1 to 2000 units of the cariogenanase enzyme per milliliter of a conventional cola drink. This would apply to the gums and teeth, in the drinking act.

EXAMPLE 15

Jet-stream teeth cleaner

To the water to be used in the conventional apparatus to deliver a high-velocity jet of water on the teeth to clean teeth, is added cariogenanase in the amount of 10–20,000 units per ml. solution.

Other formulations containing cariogenenase, and either dextranase or protease or both are included in Table I.

TABLE I

| Formulation | Cariogenanase | Dextranase | Protease |
|---|---|---|---|
| Tooth paste or powder | 5–10,000* | 50–100,000 | |
| | 5–10,000 | | 0.4–200 |
| | 5–10,000 | 50–100,000 | 0.4–200 |
| Rubbing ointment or lotion | 10–20,000 | 100–200,000 | |
| | 10–20,000 | | 0.8–400 |
| | 10–20,000 | 100–200,000 | 0.8–400 |
| Mouthwash | 1–2,000 | 10–20,000 | |
| | 1–2,000 | | 0.08–40 |
| | 1–2,000 | 10–20,000 | 0.08–40 |
| Chewing gum | 2.5–5,000 | 50–50,000 | |
| | 2.5–5,000 | | 0.02–100 |
| | 2.5–5,000 | 50–50,000 | 0.02–100 |
| Food | 1–2,000 | 10–20,000 | |
| | 1–2,000 | | 0.08–40 |
| | 1–2,000 | 10–20,000 | 0.08–40 |
| Beverage | 1–2,000 | 10–20,000 | |
| | 1–2,000 | | 0.08–40 |
| | 1–2,000 | 10–20,000 | 0.08–40 |
| Jet stream tooth cleaners | 10–20,000 | 100–200,000 | |
| | 10–20,000 | | 0.8–400 |
| | 10–20,000 | 100–200,000 | 0.8–400 |
| Lozenge | 10–20,000 units/lozenge | 100–200,000 | |
| | 10–20,000 units/lozenge | | 0.8–400 |
| | 10–20,000 units/lozenge | 100–200,000 | 0.8–400 |

*Units per ml. of liquid, or per gm. of solid unless otherwise stated.

What is claimed is:

1. A dental treating composition comprising a dental treating carrier, dextranase, and an effective amount of an enzyme capable of hydrolyzing a streptococci derived dental plaque glucan having a majority of α-(1→3)glucosidic bonds.

2. A dental treating composition comprising a dental treating carrier, dextranase, protease and an effective amount of an enzyme capable of hydrolyzing a streptococci derived dental plaque glucan having a majority of α-(1→3)glucosidic bonds.

3. A process for preparing an enzyme capable of hydrolyzing a streptococci devised dental plaque glucan having a majority of α-(1–3)glucosidic bonds which comprises:
   (a) growing a microorganism selected from the the group consisting of a fungus, NRRL No. 5305; a Streptomyces sp., NRRL No. 5306; a Streptomyces sp., NRRL no. 5307; a Streptomyces sp., NRRL No. 5308; a Streptomyces sp., NRRL No. 5309; a Bacillus sp., NRRL No. B-5300; a Bacillus sp., NRRL No. B-5301; a Bacillus sp., NRRL No. B-5302 a Bacillus sp., NRRL No. B-5303; or a Corynebacterium sp., NRRL No. B-5310; in a suitable nutrient medium.
   (b) removing insolubles from the broth; and
   (c) isolating the protein from the clarified broth, which protein comprises the desired enzyme.

4. The process of claim 3 wherein the isolated microorganism is a Bacillus sp., NRRL No. B-5300.

5. A process for preparing an enzyme capable of hydrolyzing a streptococci derived dental plaque glucan having a majority of α-(1–3)glucosidic bonds which comprises:
   (a) growing a microorganism selected from the group consisting of a fugus, NRRL No. 5305; a Streptomyces sp., NRRL No. 5306; a Streptomyces sp., NRRL No. 5307; a Streptomyces sp., NRRL No. 5308; a Streptomyces sp., NRRL No. 5309 a Bacillus sp., NRRL No. B-5300; a Bacillus sp., NRRL No. B-5301; a Bacillus sp., NRRL No. 5302; a Bacillus sp, B-5303; or a Corynebacterium sp., NRRL No. B-5310; in a suitable mutrient medium.
   (b) removing insolubles from the broth;
   (c) concentrating the clear solution;
   (d) precipitating by addition of acetone;
   (e) suspending the precipitate in a buffer and separating insolubles;
   (f) precipitating with ammonium sulfate; and
   (g) dialyzing the precipitate, which dialyzed precipitate comprises the desired enzyme.

6. The process of claim 5, wherein the isolated microorganism is a Bacillus sp., NRRL No. B-5300.

7. A process for preparing an enzyme capable of hydrolyzing a streptococci derived dental plaque glucan having a majority of α-(1–3)glucosidic bonds which comprises:
   (a) growing Bacillus sp., NRRL No. B-5300 in a suitable nutrient medium containing cariogenan as the only carbohydrate source until available cariogenan has been consumed;
   (b) removing insolubles from the broth;
   (c) concentrating the clear solution about 10 fold.
   (d) adding acetone at about −60° C. to a final concentration of about 60%;
   (e) dissolving the precipitate in a phosphate buffer of about pH 7 and separating insolubles;
   (f) adding ammonium sulfate to saturation; and
   (g) dialyzing the precipitate, which dialyzed precipitate comprises the desired enzyme.

* * * * *